United States Patent
Mordecai et al.

(10) Patent No.: US 10,022,088 B2
(45) Date of Patent: Jul. 17, 2018

(54) WEARABLE SENSOR RETAINING DEVICE

(71) Applicant: Globe Holding Company LLC, Pittsfield, NH (US)

(72) Inventors: Mark Mordecai, Hampton, NH (US); Birgit Leitner, Warwick, RI (US); Kathleen McNutt, Gilford, NH (US); Julie Snedeker, Northwood, NH (US); Karen Carter, Allenstown, NH (US); Clare King, Providence, RI (US)

(73) Assignee: Globe Holding Company, LLC, Pittsfield, NH (US)

( * ) Notice: Subject to any disclaimer, the term of this patent is extended or adjusted under 35 U.S.C. 154(b) by 902 days.

(21) Appl. No.: 14/289,089

(22) Filed: May 28, 2014

(65) Prior Publication Data
US 2014/0352023 A1 Dec. 4, 2014

Related U.S. Application Data

(60) Provisional application No. 61/827,884, filed on May 28, 2013.

(51) Int. Cl.
*A61B 5/00* (2006.01)
*A61B 5/0205* (2006.01)

(52) U.S. Cl.
CPC .......... *A61B 5/6831* (2013.01); *A61B 5/6804* (2013.01); *A61B 5/6805* (2013.01); *A61B 5/02055* (2013.01)

(58) Field of Classification Search
CPC .. A61B 5/6831; A61B 5/6804; A61B 5/02055
See application file for complete search history.

(56) References Cited

U.S. PATENT DOCUMENTS

| | | |
|---|---|---|
| 7,904,133 B2 | 3/2011 | Gehman et al. |
| 8,303,172 B2 | 11/2012 | Lei et al. |

(Continued)

FOREIGN PATENT DOCUMENTS

WO    2007040878 A1    4/2007

OTHER PUBLICATIONS

Heartshirt: A shirt that was able to detect heart sounds and display associated colors., Technovelgy, http://technovelgy.com/ct/content.asp?Bnum=295, 3 pages.

(Continued)

*Primary Examiner* — Shaun R Hurley
*Assistant Examiner* — Andrew W Sutton
(74) *Attorney, Agent, or Firm* — Finch & Maloney PLLC (57) ABSTRACT

A wearable sensor retaining device and techniques for integrating a wearable sensor retaining device into a first responder's garment, such as a firefighter's shirt. The wearable sensor retaining device may include a strap having a rigid connector having a male portion and a female portion (e.g. a side-release buckle) for adjustably securing the strap around a wearer's torso to ensure proper location of the wearable sensor and proper fit for the wearer. The strap has a portion for coupling to a wearable sensor and having sufficient tension to retain the wearable monitor in the proper location, while maintaining wearer comfort so as not to impede the range of motion of the wearer. The strap may include a length adjustment loop that provides the wearer a customized fit and quick, consistent application.

12 Claims, 8 Drawing Sheets

(56) References Cited

U.S. PATENT DOCUMENTS

| | | |
|---|---|---|
| 8,340,740 B2 | 12/2012 | Holzer et al. |
| 8,369,936 B2 | 2/2013 | Farringdon et al. |
| 2002/0032388 A1* | 3/2002 | Kristbjarnarson ... A61B 5/1135 600/538 |
| 2002/0124295 A1* | 9/2002 | Fenwick ............ A41D 13/1245 2/69 |
| 2008/0015454 A1* | 1/2008 | Gal .................... A41D 13/1281 600/509 |
| 2010/0191090 A1* | 7/2010 | Shin .................... A61B 5/0205 600/388 |
| 2011/0172503 A1* | 7/2011 | Knepper ............ A61B 5/02055 600/301 |
| 2013/0312168 A1* | 11/2013 | Raanan .............. A41D 13/0506 2/465 |
| 2014/0051938 A1* | 2/2014 | Goldstein ............ A61B 5/4818 600/301 |
| 2014/0189928 A1* | 7/2014 | Oleson ................ A61B 5/6823 2/69 |
| 2015/0174307 A1* | 6/2015 | Eckman .................. A61B 5/72 600/17 |
| 2015/0342518 A1* | 12/2015 | Persidsky .............. A61B 5/486 600/534 |

OTHER PUBLICATIONS

Men's Heart Rate Monitor Cardio Shirt, NuMetrex, Copyright 2013 Textronics, Inc., http://www.numetrex.com/about/cardio-shirt, 1 page.
Why Our Textile Sensing Technology is Better, NuMetrex, Copyright 2013 Textronics, Inc., http://www.numetrex.com/about/technical-story, 1 page.

* cited by examiner

WEARABLE SENSOR RETAINING DEVICE

RELATED APPLICATIONS

This application claims the benefit of U.S. Provisional Application Ser. No. 61/827,884, filed on May 28, 2013, the contents of which are hereby incorporated by reference herein.

STATEMENT REGARDING FEDERALLY SPONSORED RESEARCH

This invention was made in part with government support under contract W911QY-11-C-0025 awarded by U.S. Army Soldiers Systems Center on May 23, 2011. The government may have certain rights in the invention.

BACKGROUND

Field of Invention

The invention relates to safety equipment, and in particular, to a wearable sensor retaining device that may be integrated into apparel such as a shirt and used by firefighters and other first responders.

Discussion of Related Art

Firefighters and other emergency or first responders traditionally wear outer clothing known in the art as a turnout suit. The turnout suit protects the firefighter against flame, heat, and water. Typically, a turnout suit includes a coat and trousers that each have an inner liner and an outer layer. The shell or outer layer is constructed from materials that can be resistant to abrasion, flame, heat, and water. The inner liner is typically releasably secured to the outer layer to permit the liner to be removed for cleaning and repair purposes. The inner liner is preferably constructed from thermal and/or wicking materials. In addition to the turnout suit, firefighters may wear other equipment such as boots, shirt, helmet, gloves, and a self-contained breathing apparatus (SCBA).

SUMMARY OF INVENTION

One aspect of the present invention is a wearable sensor retaining device comprising: a strap passing through a channel in a garment, wherein the strap has a first end and a second end; a sensor coupling unit attached to the strap; a rigid connector comprising a male portion and a female portion, the male portion attached to the first end of the strap and the female portion attached to the second end of the strap; and a length adjustment loop integrated into the strap, wherein the length adjustment loop is a fixed length when the rigid connector is connected and when the rigid connector is disconnected.

The wearable sensor retaining device can include the length adjustment loop located at one end of the strap and the length adjustment loop can be formed from a portion of the strap and may be looped back on itself after passing through a slot on the rigid connector. The length adjustment loop can be permanently fixed to an adjustment slide that is stationary with respect to the strap when the strap is in tension. The strap may comprise some or all elastic material and can pass through a channel in a shirt. The rigid connector may be a side-release buckle and none of the connector needs to be attached to the garment with which it is used.

Another aspect of the present invention is a firefighter's ensemble comprising: a shirt; and a strap passing through a substantially horizontal channel in the shirt, wherein the strap has a first end and a second end; a sensor coupling unit attached to the strap; a rigid connector comprising a male portion and a female portion, the male portion attached to the first end of the strap and the female portion attached to the second end of the strap; and a length adjustment loop integrated into the strap, wherein the length adjustment loop is a fixed length when the rigid connector is connected and when the rigid connector is disconnected.

In some embodiments of the firefighter's ensemble the length adjustment loop is located at one end of the strap and may be permanently fixed to an adjustment slide that is stationary with respect to the strap when the strap is in tension. In one embodiment of the firefighter's ensemble, the strap comprises elastic material. In some embodiments, the shirt may also be elastic. The rigid connector can be a quick release buckle, such as a side-release buckle, and may be located outside of the horizontal channel in the shirt.

In another aspect, a method of securing a biometric sensor is provided. The method includes donning a shirt, the shirt including a sensor retaining strap passing through a horizontal channel in the shirt, connecting a rigid connector to join opposed ends of the strap together at a fixed circumference, the fixed circumference being pre-set for the size of the wearer of the sensor, and attaching a biometric sensor to the sensor retaining strap.

BRIEF DESCRIPTION OF DRAWINGS

Many features of the invention will be more readily understood by reference to the following detailed description, taken with reference to the accompanying drawings representing different embodiments, in which.

DETAILED DESCRIPTION

High risk personnel such as firefighters, defense workers and emergency responders may be exposed to hazardous conditions that can render the worker unconscious, disoriented or otherwise incapacitated. In these situations it is useful to monitor the worker's vital signs as well as his or her movement and physical position and orientation. To assure that these parameters can be monitored, emergency responders could wear a biometric sensor underneath their turnout gear or other protective clothing. However, available sensors and the devices used to hold the sensors in position can be uncomfortable and difficult to properly adjust. The wearable sensor retaining device described herein can be set to a comfortable pre-fixed length and avoids many of the problems associated with known systems. This can be accomplished, in part, by employing a strap that retains its pre-chosen length when unattached.

The wearable sensor retaining device disclosed herein may include a chest strap including a rigid connector having a male portion and a female portion (e.g. side-release buckle) for adjustably securing the strap around a wearer's torso to ensure proper location of the wearable sensor and proper fit for the particular wearer. This wearable sensor retaining device may be integrated into the inner liner of the coat of the turnout suit, or integrated into a shirt that is worn under the coat of the turnout suit. The device may be worn so that the biometric sensor is in contact with, or close to, the skin of the wearer. The strap may have a receiver for coupling to a removable wearable sensor (e.g., heart rate, respiration, pulse oximetry, temperature, accelerometer, GPS, and the like, or a combination thereof) and the strap can exhibit sufficient tension to retain the wearable monitor in the proper location while maintaining wearer comfort so as not to impede the range of motion of the wearer. The strap can include a length adjustment loop which allows for a customized fit for the wearer. The adjustment loop can provide for quick, consistent application of the wearable sensor to the wearer.

The wearable sensor retaining device disclosed herein may include a chest strap which may comprise some or all elastic material and can pass through a channel in a shirt. In certain embodiments, the elasticity of some or all of the chest strap may allow the removable wearable sensor to lie flat, to be held snugly against the body, and/or to capture vitals (e.g. respiration rate) by allowing the elastic (in some or all of the strap) to expand and contract as the chest moves when the wearer breathes. In certain embodiments, the elasticity of some or all of the chest strap allows for greater adjustability with repeated reconnects, a more secure dimension adjustment, more secure positioning on the body, ease of donning and doffing, and enhanced comfort for the wearer.

As used herein, "wearer" and "user" may be used interchangeably to denote a person wearing a wearable sensor retaining device.

Wearable sensors may be required equipment for firefighters, emergency response team members and others who may be subject to hazardous working conditions. Therefore, not only should these devices perform their safety function successfully but their everyday use means that the devices should preferably be comfortable, unobtrusive and easy to care for.

A firefighter's coat often includes both an inner liner and an outer shell. The outer shell may provide for protection against water and flame while the inner liner may protect against, for example, heat and hazardous substances. A wearable sensor retaining device may be incorporated into a coat and in some embodiments may be positioned between the shell and the inner layer. In some embodiments, the wearable sensor retaining device may be incorporated into the inner liner of the coat. In a preferred embodiment, the wearable sensor retaining device may be incorporated into a shirt worn under the coat.

The wearable sensor retaining device may be made of any appropriate material, such as, for example, polyester, nylon, KEVLAR, NOMEX, polypropylene or natural fibers. In certain embodiments, the wearable sensor retaining device will comprise at least portions that include an elastic material. The wearable sensor retaining device may be made from a single strip of material or from multiple pieces sewn or otherwise joined together. The strip of material may include ends that can be joined together to form an adjustable circumferential chest strap. A portion of the strap may include a wearable sensor coupling unit and portions of the strap may vary in width to accommodate, for example, the sensor coupling unit or a connector. One or both ends of the chest strap may include a length adjustment loop mechanism to provide proper fit to the wearer. The strap may be secured in a garment, such as a shirt, while retaining the ability to freely move in relation to the garment. For example, the strap may pass through channels in the garment that help to align the sensor at the proper height on the torso. The ends of the chest strap may include a rigid connector such as a quick-release/quick-connect buckle that can be used to connect the opposed ends of the strap to secure the wearable sensor into the proper position on the wearer. When not under strain, the wearable sensor retaining device can fit snugly under minimal tension, without gaps, around the user's chest and, in some cases, the user may not even feel that it is there.

In a preferred embodiment of the present invention, the material of the strap may be a ribbon-shaped material such as a belt. Alternatively, the material may be rounder in cross section and may be similar or identical to rope or other braided material. Embodiments described herein will be discussed with reference to ribbon-shaped material although other shapes may be equally applicable. In a preferred embodiment of the present invention, the material of the strap may be a ribbon-shaped elastic material along some or all of the length of the chest strap.

In many instances, the material can meet the requirements of a specific federal, state or organizational regulation. Although the strap may be of consistent size throughout, the width and/or thickness and/or diameter may vary at different sections of the device. The width of the material may be, for example, greater than or equal to 1 cm, 2 cm, 3 cm, 4 cm, 5 cm or more. Thickness may typically be about 1 mm, 2 mm, 3 mm, 4 mm or more. Width and thickness may be chosen, for instance, based on level of comfort and required strength. The length of the strap is typically based, at least partially, on the size of the user. Thus a wearable sensor retaining device may be custom-sized based on the size of the coat that it is to be integrated with, the size of the shirt that it is to be integrated with, and the like. For instance, size 48 turnout gear may be shipped with a wearable sensor retaining device that is six inches longer than one that is shipped with size 42.

In one embodiment, the chest strap is a continuous strap extending around the circumference of a wearer's torso. The continuous strap may comprise a single contiguous strap or may comprise multiple pieces that are stitched or otherwise fixed together. The continuous support strap may include extra length or slack, so that when it is in the relaxed position (not fastened), it can be adjusted, to provide for a customized fit for a particular user. The strap may also include a length adjustment loop passing though one of the connector portions on one end of the strap. In addition, in some embodiments, the continuous support strap may pass through loops/openings in the garment but is not fixed to the garment. In this manner, the continuous support strap can move in relation to the garment while remaining attached or linked to it.

A variety of appropriate materials for the production of straps will be apparent in light of this disclosure. Some example strap materials include polyamide, polyester, polybenzimidazole (PBI), nylon, modacrylic, aramid fibers, and/or other natural and polymeric materials, and any combinations thereof. The strap, or one or more portions of the strap, may be elastic and may expand under tension by more than 5% or more than 10% of its length. For example, a strap that is 36 inches long in its relaxed state may expand to 40 or 44 inches when the user breathes or moves. The components of the strap may be joined by various suitable methods, such as by stitching (including double or otherwise reinforced or heavy duty stitching), clamping, pressed fittings, interweaving or otherwise integrally forming the continuous strap, or combinations thereof. As will be appreciated, the present invention is not intended to be limited to a particular strap material, strap dimensions, or stitching/fixing scheme, as such details will depend on a number of factors including the target size, the given application, the desired comfort level and/or ease of use, applicable standards, and established safety and manufacturing know-how.

In a preferred embodiment, the wearable sensor retaining device may be incorporated into a garment, such as a shirt, to form a wearable sensor retaining garment. The shirt may be stretchable and may fit snugly (for example, there are no folds or gaps) around the user when in a relaxed state but may expand circumferentially by more than 5% or more than 10% without restricting the movement or breathing of the user. In one embodiment described herein, the wearable sensor retaining device may pass through one or more channels in the garment and may include a fixed loop at one end of the strap. A "fixed" loop is one in which the loop (e.g. a length adjustment loop) is designed to retain its size once a size has been set by the user. The strap can be disconnected and reconnected without altering the size of the connected strap. The length of the strap can be adjusted easily when the ends of the strap are not joined together. However, once the ends are joined together, the length of the strap is stable and remains of fixed length. The fixed loop remains adjustable to customize the fit to a particular user such that the wearable sensor remains in the proper position for optimal performance and comfort. In a further embodiment, the strap may be passed through a channel in the garment and may be slidably retained by the channel although in some embodiments that strap can be removed from the channel to facilitate, for instance, laundering of the garment. In this manner, the proper configuration of the wearable sensor retaining device may be maintained while allowing the device to be serviced and/or inspected.

In one set of embodiments, the strap may be integrated into the garment such that an opening in the garment that accommodates the strap is reinforced. The opening may be at one or more ends of a channel. In one embodiment, two or more pieces of reinforcing material may be affixed to the edges of an opening in a garment to provide a reinforced opening and/or channel. The two pieces of reinforcing material may be identical or almost identical and may be stitched to opposing edges of a slit that defines the channel opening. In one embodiment, the method of reinforcing an opening may include, stitching, adding material, or both. Reinforcing material may be any type of material that can be sewn or otherwise affixed to an opening in the garment to improve the wear characteristics of the opening and may be a material that is resistant to fraying. Coated materials, such as those coated with a high solid polymer, may be preferred. Materials used for reinforcement may include polymeric and non-polymeric materials, for example, natural fibers, leather, nylon, polyester, and aromatic polyamides (aramid and para-aramids fibers) such as KEVLAR. Blends of these and other materials may also be used.

In one aspect, a wearable sensor retaining device is provided that may be used in conjunction with apparel, such as a shirt. The shirt may have short sleeves, long sleeves, or no sleeves. In some embodiments, the wearable sensor retaining device may have a strap or straps that are capable of sliding horizontally without significantly altering the positioning of the wearable sensor around the wearer's torso. Such a wearable sensor retaining device can be, for example, simple to use, expandable, non-constricting, and generally provide a greater level of comfort to the wearer while maintaining adequate contact with the wearer to receive important data, such as respiration and heart rate. The wearable sensor retaining device may be worn inside of firefighter apparel, or may be integrated into firefighter apparel. In some such cases, the wearable sensor retaining device may be fully or partially integrated with firefighter's coat. In certain embodiments, the wearable sensor retaining device may be fully or partially integrated into a shirt.

In some embodiments, the garment may be constructed of materials including, but not limited to, cotton, polyester, rayon, spandex, jersey, tricot, and the like. In certain embodiments, the materials may have a variety of properties depending on the application. Some material properties may include moisture wicking, stretching, breathability, and the like. The material may be breathable and in some embodiments can allow the transmission of water vapor at a rate of greater than 100 g/m$^2$/day.

In some embodiments, the chest strap of the wearable sensor retaining device is essentially of a fixed circumference (i.e. it does not change) due, in part, to the fixed loop located on one end of the strap even though the strap may be comprised, at least in part of elastic material. Such straps of fixed circumference can be provided, for example, in varying sizes such as small, medium, and large to accommodate most users. In certain embodiments, however, the length can be adjusted when the wearable sensor retaining device is not fastened, typically with adjustable buckles, clips, clamps, or other such suitable mechanisms for adjusting straps and the like. Once the strap has been adjusted, it can be fastened and can provide a customizable, secure fit for a particular user. The "fit" may then be retained for each successive use of the device by that user with no additional adjustment being necessary. When the opposed ends of the strap are joined, the length of the strap will be identical to its length when the ends were joined the previous time. This is in contrast to many systems where securing and length adjustment involve the same step.

Figure 1A:
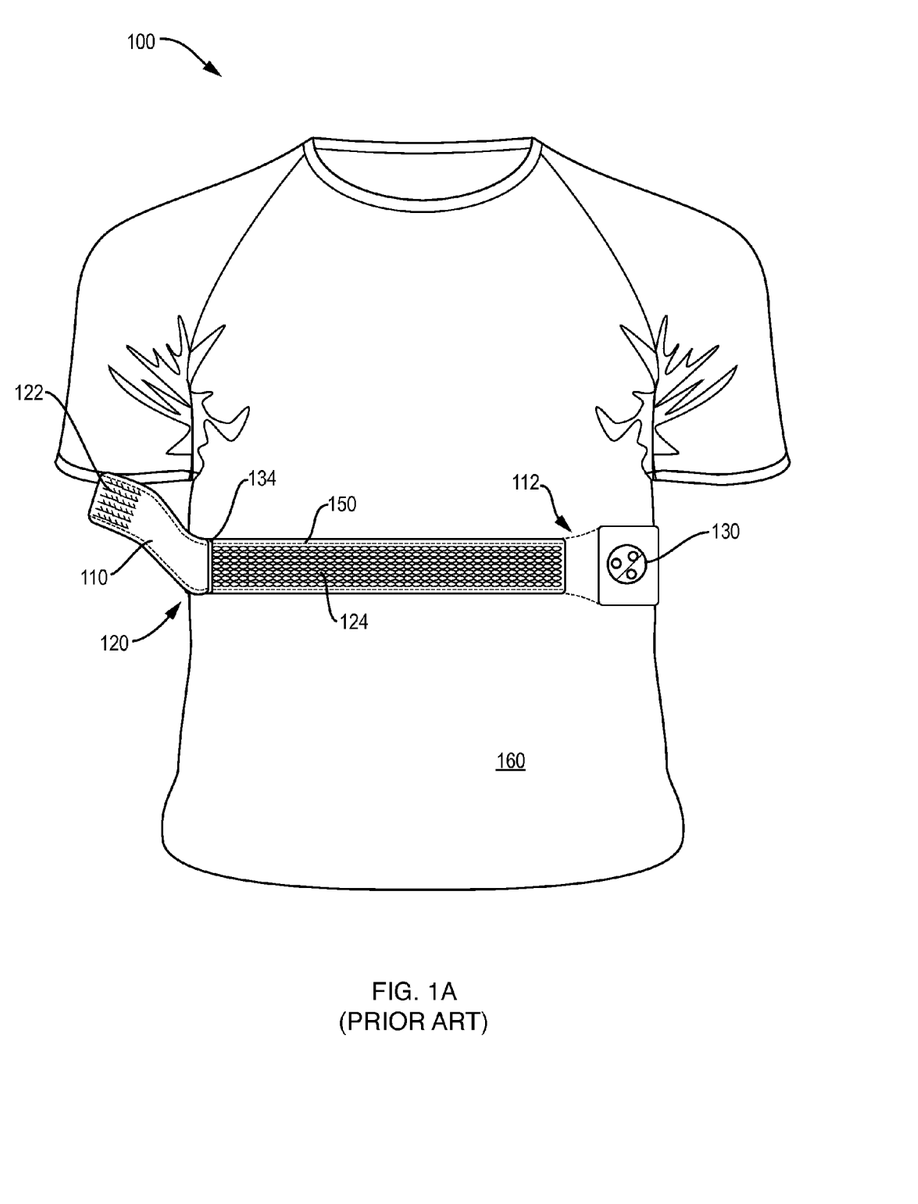
FIGS. 1A and 1B provide front views of a wearable sensor retaining device of the prior art.
Figure 1B:
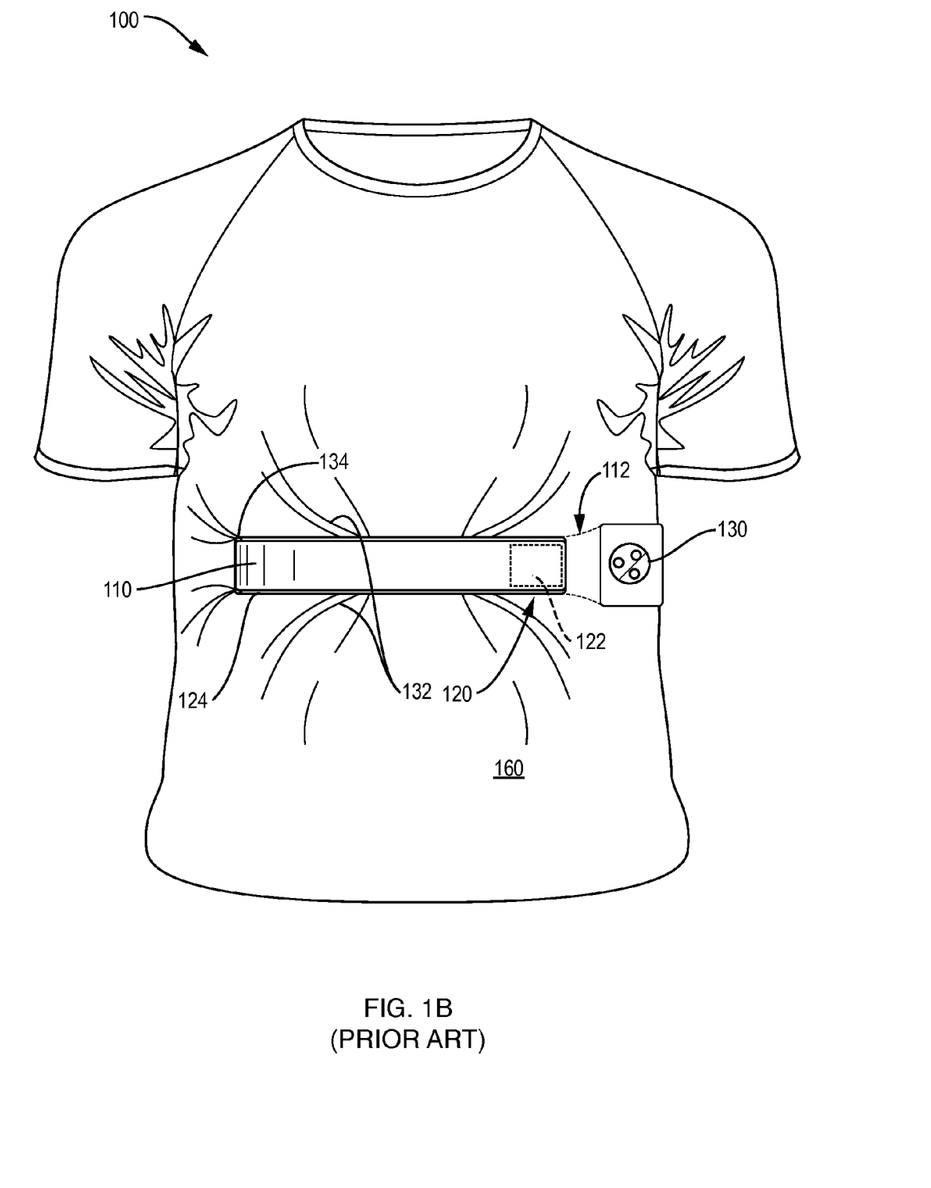

FIGS. 1A and 1B provide front views of a known wearable sensor retaining garment 100. Particularly, a shirt 160 is shown having an attached wearable sensor retaining device 112. In FIG. 1A, hook and loop securing mechanism 120 is unfastened and in FIG. 1B securing mechanism 120 has been tightened and fastened. Wearable sensor retaining device 112 includes a strap 110, and a hook and loop securing mechanism 120 that is permanently sewn into or onto shirt 160 so as to retain a wearable sensor receiver 130 in position against the wearer's body. Hook and loop securing mechanism 120 includes hook portion 122 at the free end of strap 110 and loop portion 124 at the opposite end of strap 110. Strap 110 emerges from the shirt 160 via slit 134 in loop portion 124. Thus, strap 110 can be tightened by pulling hook portion 122 through slit 134 while loop portion 124 stays substantially stationary with reference to shirt 160. The entirety of loop portion 124 is secured to shirt 160 via stitching 150. In FIG. 1A, hook and loop securing mechanism 120 is unfastened and both loop portion 124 and shirt 160 are substantially unwrinkled. To secure strap 110, hook portion 122 is pulled through slit 134 and back onto loop portion 124 to both secure the strap as well as fix its length or circumference.

As seen in FIG. 1B, strap 110 has been tightened by pulling hook portion 122 across the chest and attaching it to loop portion 124 at a location close to wearable sensor receiver 130. This cinches device 112 tightly around the wearer but in doing so puts one or more folds 132 in strap 110 at loop portion 122. As loop portion 122 is sewn to shirt 160, the shirt is also folded back on itself and can become uncomfortable under the compression of the wearable sensor retaining device 112. The circumference of the strap around the user is set every time by the user when the strap is secured. There is no indication if the length of the strap is the same as when it was secured a previous time.

Figure 2:
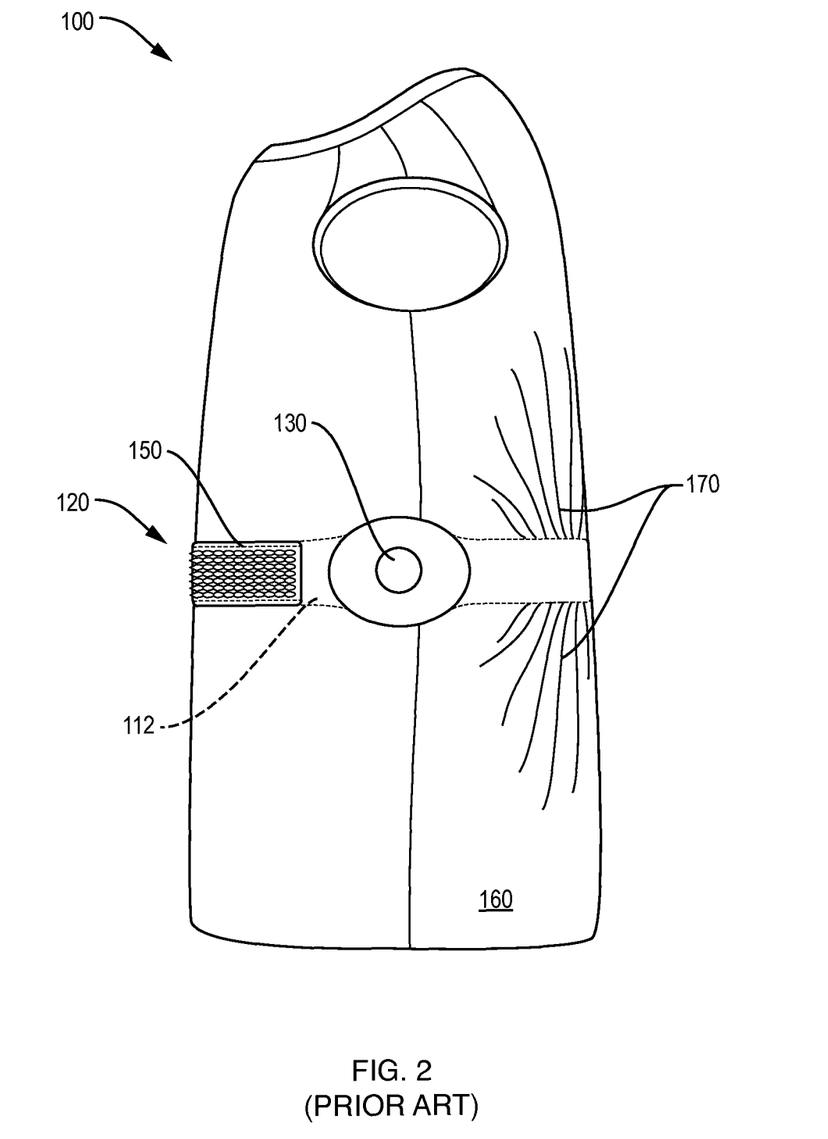
FIG. 2 provides a left side view of a wearable sensor retaining device of the prior art.
Figure 3:
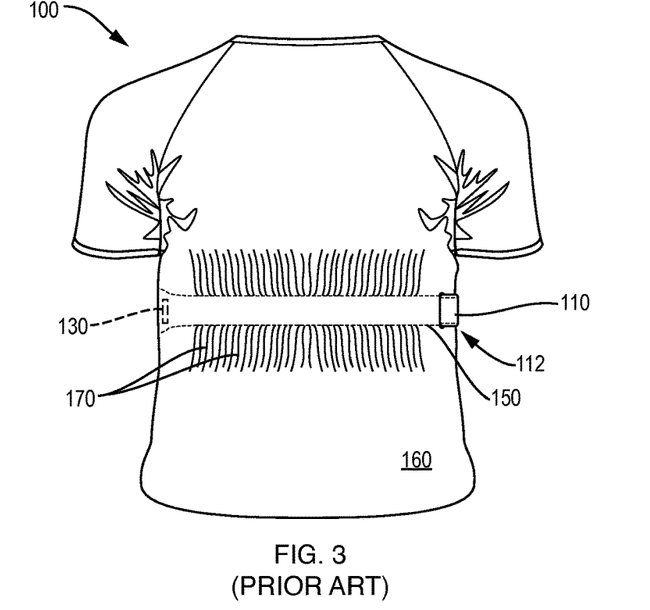
FIG. 3 provides a back view of a shirt including a wearable sensor retaining device of the prior art.
Figure 4:
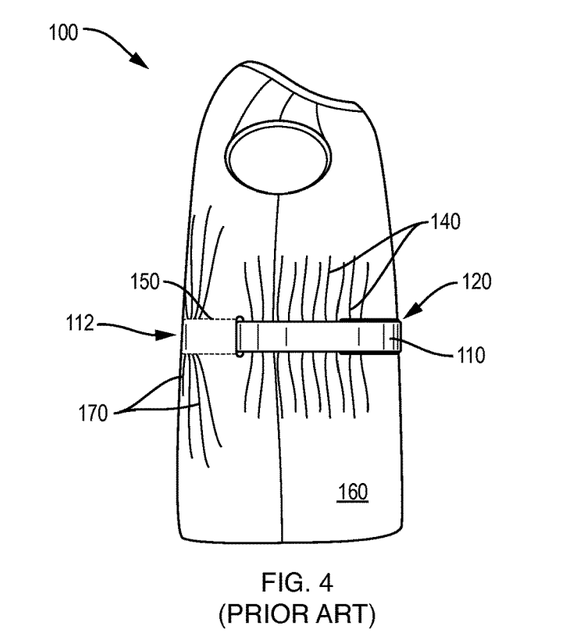
FIG. 4 provides a right side view of a shirt including a wearable sensor retaining device of the prior art.

FIG. 2 provides a left side view of a wearable sensor retaining garment 100 of the prior art. More specifically, the wearable sensor retaining device 112 comprises a securing mechanism 120 (e.g. Velcro hook and loop) that is sewn with stitching 150 into or onto a shirt 160 so as to retain a wearable sensor receiver 130 in position against the wearer's body. As seen in FIG. 2, prior art wearable sensor retaining devices are bulky and create multiple folds 170 in the fabric along the back of the shirt when fastened. FIG. 3 provides a back view of a wearable sensor retaining device 112 of the prior art. As seen in FIG. 3, the folds 170 in the fabric extend along the back of the shirt when adjusted to the size of a particular wearer. FIG. 4 provides a right side view of a wearable sensor retaining device 112 of the prior art. As can be seen in FIG. 4, the folds 140 in the fabric extend along the right side of the shirt 160 when adjusted to the size of a particular user.

Figure 5:
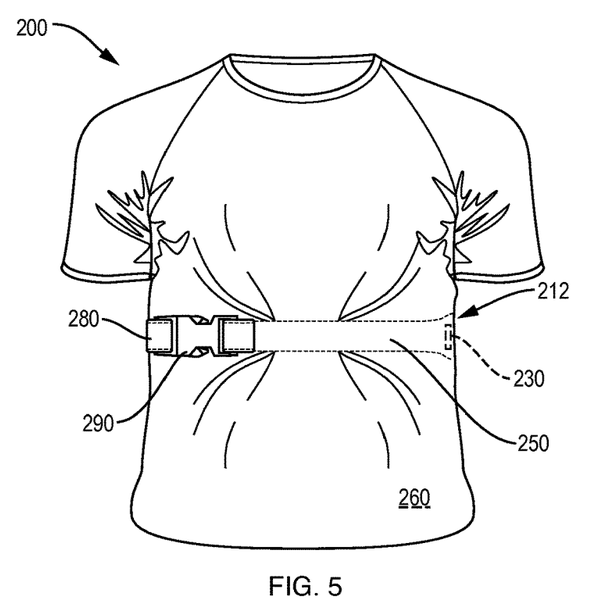
FIG. 5 provides a front view of a wearable sensor retaining device positioned on the user's torso, in accordance with an embodiment of the present invention.

FIG. 5 provides a front view of a wearable sensor retaining device 212, in accordance with an embodiment of the present invention. More specifically, the wearable sensor retaining device 212 incorporated into a garment 260 provides for a wearable sensor retaining garment 200. The wearable sensor retaining device 212 comprises a wearable sensor coupling unit 230 incorporated therein. As can be seen in FIG. 5, in one embodiment of the present invention, a strap 280 is incorporated into the garment 260 such that the garment retains a relatively smooth profile and the strap 280 is in a channel 250 of the garment 260. Although portions of strap 280 may be sewn or otherwise affixed to garment 260, the two opposed ends of strap 280 are free of garment 260. The wearable sensor retaining device 212 may have a quick-connect/quick-release fastening mechanism 290 used for quickly and reproducibly securing the wearable sensor into position on a particular wearer. This quick-connect/quick-release fastening mechanism may take any form known to those of skill in the art, including a rigid connector, such as a two piece buckle comprising a deformable male portion and a female portion.

Figure 6:
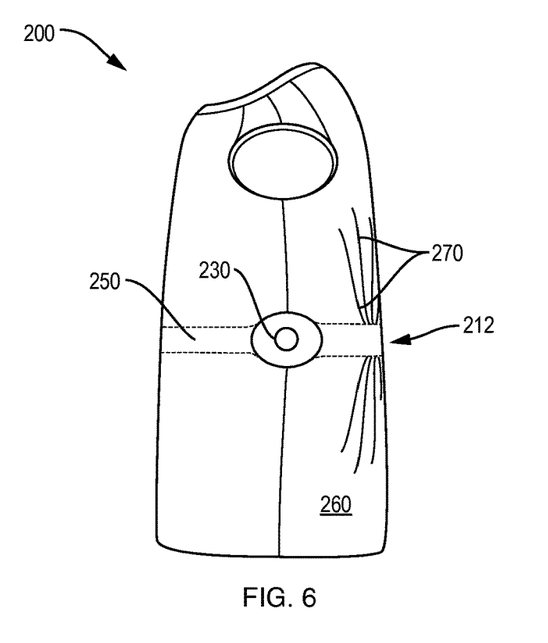
FIG. 6 provides a left side view of a wearable sensor retaining device positioned on the user's torso, in accordance with an embodiment of the present invention.

FIG. 6 provides a left side view of a wearable sensor retaining device 212 in accordance with one embodiment of the present disclosure. As can be seen in FIG. 6, there is a relatively smooth profile to the garment 260 when fastened. When the strap is fastened into position there may or may not be wrinkles in fabric 270, which, if present at all, are evenly distributed across the back of the garment 260. This is a result of, at least partially, the independence of the ends of strap which, unlike the prior art, are not stitched to the garment 260 and can be tightened independently of the garment. It can be appreciated that the choice of material for the garment 260 (e.g. stretchable) may also eliminate wrinkles in an embodiment of a wearable sensor retaining device 212 of the present invention. For example, garment 260 may be made from a stretchable fabric that stretches at about the same rate as strap 280.

By releasing quick-connect/quick-release fastening mechanism 290 as seen in FIG. 5, the garment becomes loose and can be removed easily. When the wearer needs to wear the garment again, the fastening mechanism 290 need only be reconnected and the wearable sensor will be in the proper position. As can be appreciated, firefighters, first responders, and the like require equipment that can be utilized very quickly and cannot tolerate devices that are cumbersome or difficult to position correctly.

Figure 7:
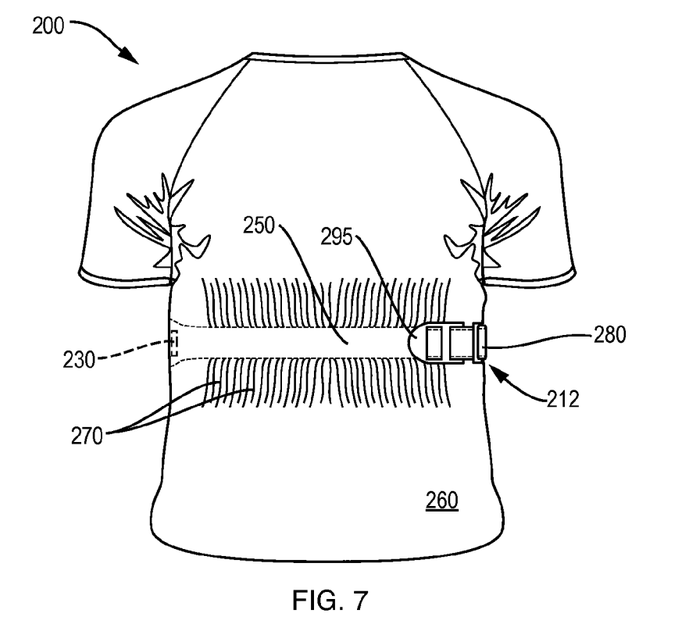
FIG. 7 provides a back view of a wearable sensor retaining device positioned on the user's torso, in accordance with an embodiment of the present invention.

FIG. 7 provides a back view of a wearable sensor retaining device 212 in accordance with an embodiment of the present invention. As can be seen in FIG. 7 (see also FIG. 10), there is an adjustment mechanism 295 (e.g. to create the length adjustment loop) present on the strap 280, which allows a wearer to adjust the size of the strap for their specific chest circumference. As shown, the circumference of strap 280 can be adjusted when the strap is disconnected. One benefit of this can be that the act of tightening strap 280 does not compress and/or put folds in garment 260. As can also be seen, when the strap is fastened into position there may or may not be wrinkles in fabric 270, which, if present at all, are evenly distributed across the back of the garment 260 and not present as large folds under the hook and loop fastener as in the prior art. This provides the wearer with a comfortable garment that will not bunch up or obstruct the free range of motion of the wearer.

Figure 8:
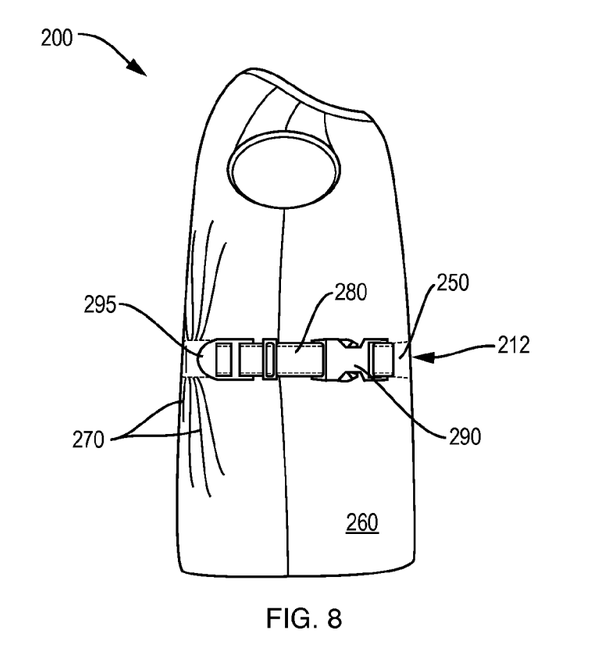
FIG. 8 provides a right side view of a wearable sensor retaining device positioned on the user's torso, in accordance with an embodiment of the present invention.

FIG. 8 provides a right side perspective view of wearable sensor retaining device 212 in accordance with an embodiment of the present invention. This Figure, when compared to that of FIG. 4, illustrates one of the differences in the wearable sensor retaining device disclosed herein. In the embodiment of FIG. 8, there is a fastening mechanism 290 that has a low profile and is able to connect opposed ends of strap 280 without attaching the mechanism to the garment itself. This can help to distribute any excess fabric around the circumference of the user evenly—not simply bunched up under the hook and loop fastener. In one embodiment, the strap 280 is of a fixed (but stretchable) circumference. This reduces any bunching around the wearer and still provides enough room for the wearer to comfortably put the garment on and tighten it for use without a large number of cumbersome folds in the connecting region of the device.

Figure 9:
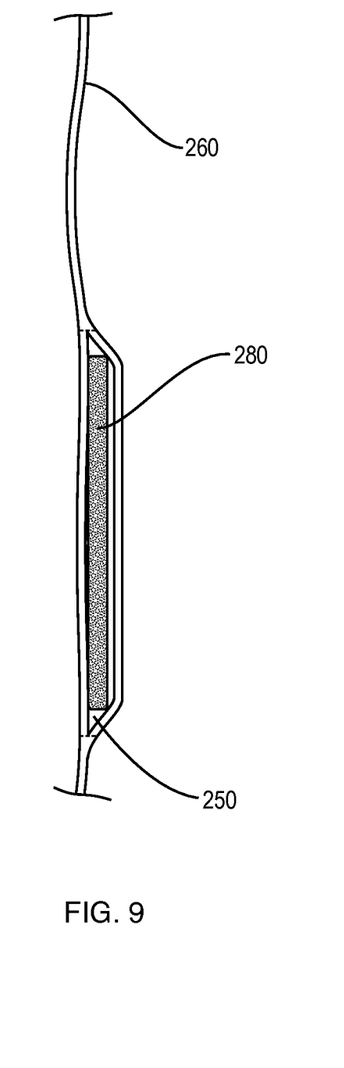
FIG. 9 provides a cross-sectional view of a channel in a shirt, in accordance with an embodiment of the present invention.

FIG. 9 provides a perspective view of a channel in accordance with an embodiment of the present invention. More specifically, the garment 260 may include a channel 250 that at least partially surrounds the strap 280. The channel 250 may be reinforced throughout its length, at any openings, or not at all. The channel 250 may extend around only a portion of the garment, or around the circumference of the garment. The channel 250 may be formed by stitching additional material onto the garment, or by creating a fold in the garment, or the like, depending on the application. The channel 250 can provide a barrier between strap 280 and the wearer's body as well as a barrier between strap 280 and the environment.

Figure 10:
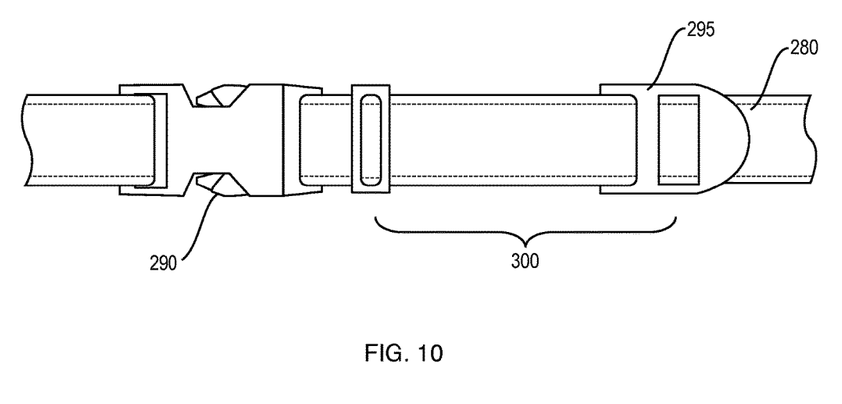
FIG. 10 provides a perspective view of a length adjustment loop and rigid connector, in accordance with an embodiment of the present invention.

FIG. 10 provides a perspective view of a length adjustment loop 300 in accordance with an embodiment of the present invention. More specifically, length adjustment loop 300 is formed from an end portion of strap 280 and is thus integral to strap 280. In certain embodiments, the length adjustment loop 300 is formed by threading strap 280 through the adjustment mechanism 295, through fastening mechanism 290 and back to adjustment mechanism 295 where the end of strap 280 can be sewn onto itself, permanently attaching strap 280 to adjustment mechanism 295. As length adjustment loop 300 is lengthened by separating fastening mechanism 290 and adjustment mechanism 295, the circumference of strap 280 around the user is shortened. Once the strap has been adjusted to fit a particular user, the loop 300 can remain at the same fixed length whether the fastening mechanism 290 is connected or disconnected, providing a reproducible, customizable fit for each wearer.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

The foregoing description of the embodiments of the invention has been presented for the purposes of illustration and description. It is not intended to be exhaustive or to limit the invention to the precise form disclosed. Many modifications and variations are possible in light of this disclosure.

It is intended that the scope of the invention be limited not by this detailed description, but rather by the claims appended hereto.

What is claimed is:

1. A wearable sensor retaining device comprising:
    a strap passable through a channel in a garment, wherein the strap has a first end and a second end;
    a sensor coupling unit attached to the strap;
    a rigid connector comprising a male portion and a female portion, the male portion attached to the first end of the strap and the female portion attached to the second end of the strap; and
    a length adjustment loop integrated into the strap and permanently fixed to an adjustment slide, wherein the adjustment slide is stationary with respect to the strap when the strap is in tension and the length adjustment loop is a fixed length when the male portion and the female portion are connected and when the male portion and the female portion are disconnected.

2. The wearable sensor retaining device of claim 1, wherein the length adjustment loop is a portion of the strap and may be looped back on itself after passing through a slot on the rigid connector.

3. The wearable sensor retaining device of claim 1, wherein the strap comprises elastic material.

4. The wearable sensor retaining device of claim 1, wherein the rigid connector comprises a side-release buckle.

5. The wearable sensor retaining device of claim 1 wherein the strap is passable through a channel in a stretchable shirt.

6. The wearable sensor retaining device of claim 1, wherein the entire rigid connector is not fixed to the garment.

7. A firefighter's ensemble comprising:
    a shirt;
    a strap passing through a substantially horizontal channel in the shirt, the strap having a first end and a second end;
    a sensor coupling unit attached to the strap;
    a rigid connector comprising a male portion and a female portion, the male portion attached to the first end of the strap and the female portion attached to the second end of the strap; and
    a length adjustment loop integrated into the strap and permanently fixed to an adjustment slide, wherein the adjustment slide is stationary with respect to the strap when the strap is in tension and the length adjustment loop is a fixed length when the rigid connector is connected and when the rigid connector is disconnected.

8. The firefighter's ensemble of claim 7, wherein the length adjustment loop is located at one end of the strap.

9. The firefighter's ensemble of claim 7, wherein the strap comprises elastic material.

10. The firefighter's ensemble of claim 7, wherein the rigid connector comprises a side-release buckle.

11. The firefighter's ensemble of claim 7, wherein the sensor coupling unit and the rigid connector are on an external side of the shirt and are external to the horizontal channel.

12. The firefighter's ensemble of claim 7 wherein the shirt and the strap are both at least partially elastic.

\* \* \* \* \*